US00PP30417P3

(12) United States Plant Patent
Randag

(10) Patent No.: US PP30,417 P3
(45) Date of Patent: Apr. 16, 2019

(54) CALLA LILY PLANT NAMED 'BLOODY MARY'

(50) Latin Name: *Zantedeschia sprengeri*
Varietal Denomination: Bloody Mary

(71) Applicant: Dümmen Group B.V., De Lier (NL)

(72) Inventor: Cecilius Jan-Jochem Randag, 't Zand (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/732,647

(22) Filed: Dec. 7, 2017

(65) Prior Publication Data

US 2018/0177111 P1 Jun. 21, 2018

Related U.S. Application Data

(60) Provisional application No. 62/498,157, filed on Dec. 15, 2016.

(51) Int. Cl.
*A01H 5/02* (2018.01)

(52) U.S. Cl.
USPC ..... Plt./490
CPC ..... *A01H 5/02* (2013.01)

(58) Field of Classification Search
USPC ..... Plt./490
See application file for complete search history.

*Primary Examiner* — Annette H Para
(74) *Attorney, Agent, or Firm* — The Webb Law Firm

(57) ABSTRACT

'Bloody Mary' is a new variety of calla lily plant having inflorescences with a red-colored spathe that produces 2-10 inflorescences per tuber. The height of the top of an inflorescence above the soil can reach up to 48 cm. The leaves are green with transparent maculations present and have a leathery texture.

1 Drawing Sheet

Botanical classification: *Zantedeschia sprengeri.*
Varietal denomination: 'Bloody Mary'.

BACKGROUND OF THE NEW PLANT

The present invention comprises a new and distinct cultivar of calla lily, botanically known as *Zantedeschia sprengeri* and hereinafter referred to by the cultivar name 'Bloody Mary'.

'Bloody Mary' is a product of a planned breeding program, which had the objective of creating *Zantedeschia* hybrids for pot flower production in a wide range of colors with a large, classic flower shape. The breeding program began in 1989, and the new cultivar is a seedling selected from the crossing of a *Zantedeschia sprengeri* selection referred to as Z071902 (female parent, unpatented) with a *Zantedeschia sprengeri* selection referred to as Z071428-945 (male parent, unpatented). 'Bloody Mary' was selected in 2011 by the inventor in 't Zand, The Netherlands as one flowering plant within the progeny of the stated cross.

The first act of asexual reproduction of 'Bloody Mary' by tissue culture was performed by the inventor in September of 2011 in 't Zand, The Netherlands. Subsequent asexual reproductions by tissue culture at the same location have demonstrated that the combination of characteristics as herein disclosed for the new cultivar are retained and reproduced true to type through successive generations of asexual reproduction.

The following observations, measurements and comparisons describe plants grown from 12-14 weeks in 14 cm pots in 't Zand, The Netherlands under greenhouse conditions, which approximate those generally used in horticultural practice. Color references are made to the 2001 R.H.S. Colour Chart of The Royal Horticultural Society of London, except where general color terms of ordinary significance are used.

The present invention has not been evaluated under all possible environmental conditions. The phenotype may vary with variations in environment without a change in the genotype of the plant.

The following traits have been repeatedly observed and determined to be basic characteristics of 'Bloody Mary' which, in combination, distinguish this calla lily as a new and distinct cultivar:

1. Red-colored spathes;
2. Large inflorescences; and
3. High inflorescence production.

Further, when compared to calla lily plant named 'Red Charm' (U.S. Plant Pat. No. 27,822), the upper surface spathe color of 'Red Charm' varies between Greyed-Purple Group RHS 187B and 187C, whereas the upper surface spathe color of 'Bloody Mary' varies between Red Group RHS 45A and 53B, with a secondary color that varies between Yellow Group RHS 6A and 7B.

Table 1 provides similarities and differences of 'Bloody Mary' to its parents, *Zantedeschia sprengeri* selection Z071902 and *Zantedeschia sprengeri* selection Z071428-945.

TABLE 1

| 'Bloody Mary' | Similarities | Differences |
|---|---|---|
| Z071902 | Plant height | Spathe color |
| | Number of inflorescences | Spathe shape |
| Z071428-945 | Leaf shape | Number of inflorescences |
| | Spathe size | Plant height |
| | Spathe color | Leaf shape |

BRIEF DESCRIPTION OF THE DRAWING

The accompanying photographic drawing illustrates the new variety, with the colors being as nearly true as is possible with color illustrations of this type:

FIG. 1 is a photograph of a plant of the new variety.

DESCRIPTION OF THE NEW PLANT

The plant:

*Size.*—Height of the leaf canopy above the soil: 9-40 cm. Height of top of inflorescences above the soil: 21-48 cm. Diameter: 6-8.5 cm.

*Form.*—Erect.

*Number of inflorescences per tuber.*—Size 14-16 cm in diameter: 2-6 inflorescences. Size 16-18 cm in diameter: 3-7 inflorescences. Size 18-20 cm in diameter: 4-8 inflorescences. Size 20+ cm in diameter: 6-10 inflorescences.

*Branches.*—Average Number: 9.3. Color: Between Yellow-Green Group RHS 144A and 144B.

*Leaves.*—Size: Width: 4-11.5 cm. Length: 14-21 cm. Number per plant: 20-29. Shape: Lanceolate. Apex: Apiculate. Base: Between sagittate and truncate. Margin: Undulate; having a color between Yellow-Green Group RHS 146A and 147B. Color: Upper surface: Green Group RHS 137A to Yellow-Green Group RHS 147B, having transparent maculations of approximately White Group RHS 155A. Lower surface: Yellow-Green Group RHS 146A to 147B, having transparent maculations of approximately White Group RHS 155A. Veins: Configuration: Pinnate. Color: Upper Surface: Yellow-Green Group RHS 149A to 154D. Lower Surface: Green Group RHS 137A. Surface quality: Leathery. Petiole: Length: 3-25 cm. Diameter: 3-8 mm. Color: The base is White Group RHS 155A, the upper part is Yellow-Green Group RHS 144A to 144B.

*Roots.*—Color: White. Branching: Similar to other *Zantedeschia* varieties.

The inflorescence and seeds:

*Spathe.*—Size: Length (measured from opening to tip): 6-9 cm. Width: 4.5-6 cm. Height: 6-12 cm. Color: Upper surface: Varies between Red Group RHS 45A and 53B, with a secondary color that varies between Yellow Group RHS 6A and 7B. Lower surface: Varies between Orange-Red Group RHS N34A and Red Group RHS 46B, with a secondary color that varies between Yellow Group RHS 6A and 7B. Vein color: Between Orange-Red Group RHS N34A and Green Group RHS 143B. Shape: Funnel. Apex: Apiculate. Base: Attenuate. Margin: Undulate. Texture: Smooth (upper and lower surfaces).

*Spadix.*—Size: Length: 28-42 mm. Diameter: 5-9 mm. Color: Between Yellow Group RHS 13A and Yellow-Orange Group RHS 14A. Position relative to spathe: Upright.

*Peduncle.*—Size: Length: 15-36 cm. Diameter: 5-9 mm. Color: The upper part is between Green Group RHS 137A and Yellow-Green Group RHS 144A, the lower part is Green-White Group RHS 157C. Texture: Smooth.

*Reproductive organs.*—Location of female organs: Basal position of the spadix. Location of male organs: Upper position of the spadix. Perianth: Conspicuous. Stamens: Presence: Not visible before pollen release. Number: More than 20. Pollen amount: Abundant; similar to 'Picasso' (U.S. Plant Pat. No 15,282). Color: Between White Group RHS 155A and 155B. Anther: Shape: Round. Length: Less than 1 mm. Color: Between Yellow Group RHS 13A and 14A. Filament: Length: Less than 1 mm. Color: Between White Group RHS 155A and 155B. Pistils: Number: 15 to 30. Length beyond perianth: About 1 mm. Stigma: Shape: Round. Size: Less than 1 mm. Style: Length: Less than 1 mm. Color: Between Yellow Group RHS 12C and Yellow-Orange Group RHS 15C. Ovaries: Texture: Smooth. Length: Between 1 to 10 mm. Width: Between 1 to 10 mm. Color: Top color is between Yellow-Green Group RHS N144D and 154C, the bottom color is between White Group RHS 155B to Green-White Group RHS 157C.

*Seeds.*—Length: 4-7 mm. Width: 3-6 mm. Color: Between Yellow-Green Group RHS 150A and 151A. Amount: Between 1-60.

General:

*Disease resistance.*—No unusual susceptibility to diseases noticed to date.

*Pest resistance.*—No unusual susceptibility to pests noticed to date.

*Heat tolerance.*—No heat tolerance.

*Hardiness.*—Not hardy.

*Flowering.*—In general, the time from planting to first flowering takes eight weeks. However, tubers stored for a longer period before planting may flower earlier — up to five weeks after planting.

*Lastingness.*—About two weeks on the plant.

*Fragrance.*—None.

I claim:

1. A new and distinct variety of calla lily plant named 'Bloody Mary' as herein described and illustrated.

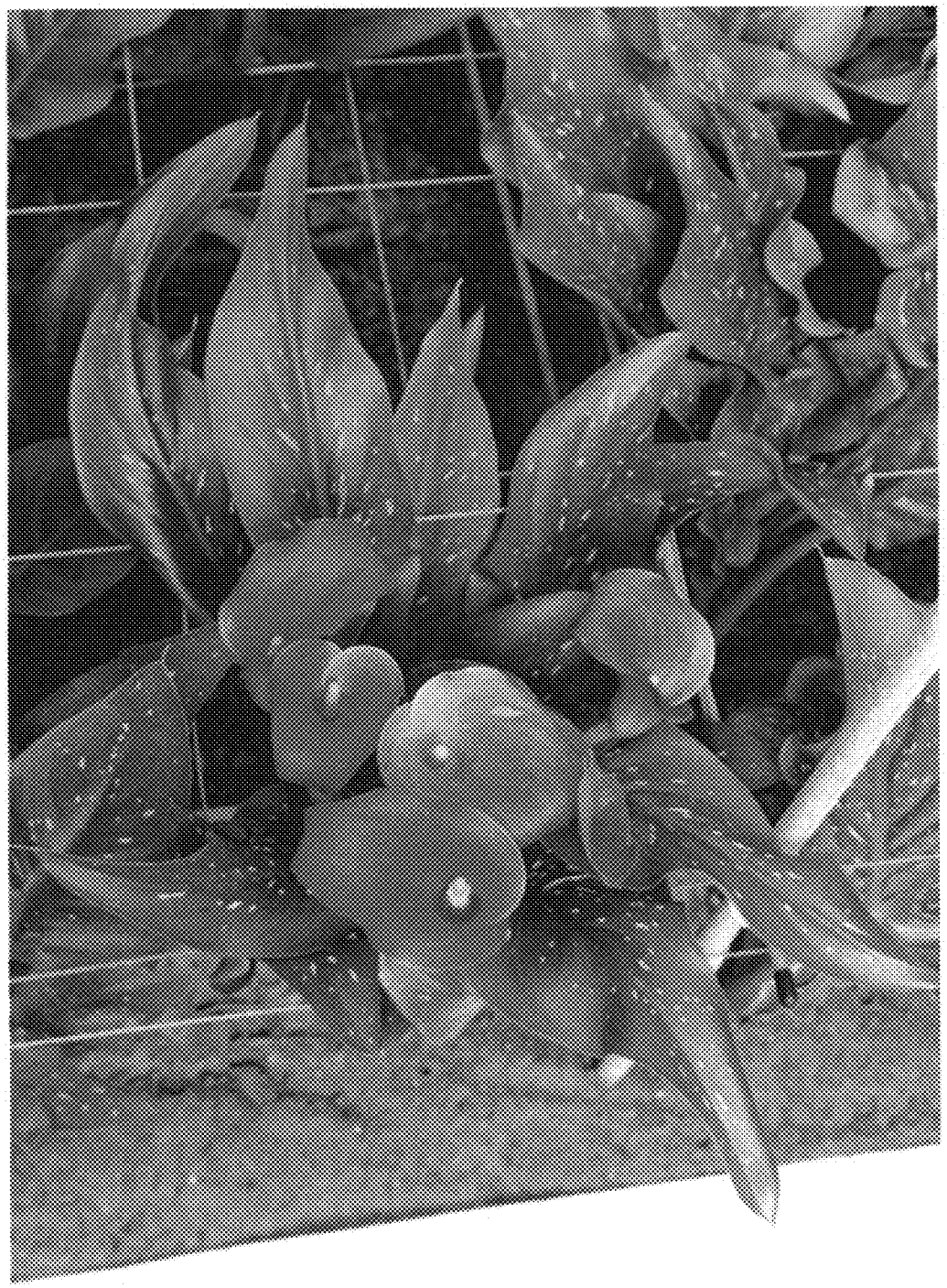

* * * * *